United States Patent [19]

Gilliand et al.

[11] 4,056,921
[45] Nov. 8, 1977

[54] ASEPTIC PACKING UNIT AND A SERVICE UNIT FOR PROVIDING THE PACKING UNIT WITH STERILE UTILITIES

[75] Inventors: André Ferdinand Louis Gilliand, Rorschacherberg; Christian Looser, Lutzenberg, both of Switzerland

[73] Assignee: Alcan Research and Development Limited, Montreal, Canada

[21] Appl. No.: 628,322

[22] Filed: Nov. 3, 1975

[30] Foreign Application Priority Data

Nov. 5, 1974 Switzerland .................... 014799/74

[51] Int. Cl.$^2$ .................. B08B 13/00; B65B 17/00; B65B 55/04; B65B 55/12
[52] U.S. Cl. .................................. 53/167; 21/103; 21/61; 53/86; 99/484; 134/102
[58] Field of Search .................. 21/61, 78, 80, 103; 134/18, 42, 94, 102; 23/259; 99/484, 356; 53/167, 86; 141/85; 426/399–402, 407

[56] References Cited

U.S. PATENT DOCUMENTS

| | | | |
|---|---|---|---|
| 1,531,808 | 3/1925 | Parkinson | 21/61 |
| 1,934,826 | 11/1933 | Shepherd | 21/78 |
| 2,121,361 | 6/1938 | Marran | 134/94 |
| 2,367,393 | 1/1945 | Green | 53/167 |
| 2,571,575 | 10/1951 | Holmes | 134/102 |
| 2,919,070 | 12/1959 | Arant | 134/18 |
| 2,948,479 | 8/1960 | Graceman | 134/102 |
| 3,035,886 | 5/1962 | Hickey | 426/399 |
| 3,055,403 | 9/1962 | Barresi | 53/167 |
| 3,392,034 | 7/1968 | Barnes | 21/78 |
| 3,566,575 | 3/1971 | Lisiecki | 53/167 |
| 3,747,296 | 7/1973 | Zausner | 21/80 |
| 3,797,744 | 3/1974 | Smith | 134/102 |
| 3,810,787 | 5/1974 | Yoeli et al. | 134/100 |
| 3,891,779 | 6/1975 | Robinson | 426/399 |
| 3,902,877 | 9/1975 | Swaim | 21/78 |
| 3,912,535 | 10/1975 | Rauser | 53/167 |

Primary Examiner—Morris O. Wolk
Assistant Examiner—Bradley Garris
Attorney, Agent, or Firm—Cooper, Dunham, Clark, Griffin & Moran

[57] ABSTRACT

A service unit capable of supplying sterile utilities including compressed air and water and preferably both hot and cold water, disinfectant and suction, is particularly adapted to be connected to machines for the packaging of foods, medicines and the like under aseptic conditions to provide servicing utilities. The service unit has the advantage of being capable of supplying sterile utilities to such aseptic packaging machines from outside the aseptic screen surrounding the packaging workspace and thus to be capable of providing sterile services to several packaging machines in turn.

3 Claims, 5 Drawing Figures

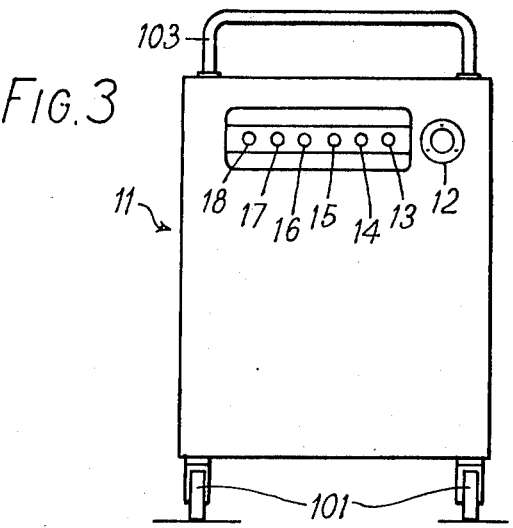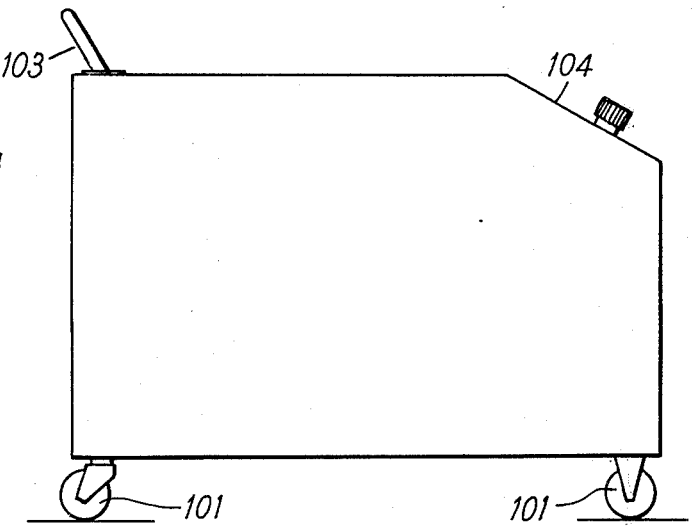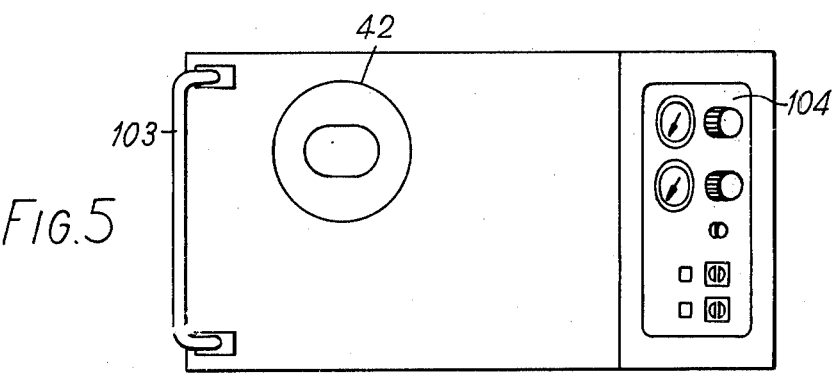

ASEPTIC PACKING UNIT AND A SERVICE UNIT FOR PROVIDING THE PACKING UNIT WITH STERILE UTILITIES

The present invention relates to a unit for servicing equipment operating in a workspace within a controlled environment where it is important to avoid contaminating the workspace from outside. Particularly, the invention relates to servicing low-germ or preferably aseptic workspaces such as are used in packaging aseptic products.

The technique of aseptic packaging involves preparing a germ free container and filling it with germ free contents and sealing a cover onto it in an environment. The technique is applied to pharmaceutical and medical products and has been developed for packaging foods which are particularly susceptible to infection by pathogenic micro-organisms or contamination by putrefying micro-organisms. The technique is used in packaging milk and milk based foods such as cream and yoghurt because these materials are particularly susceptible to proliferation of micro-organisms.

Typically an aseptic packaging plant provides an aseptic workspace effectively sealed against micro-biological contamination from the outside atmosphere. This can conveniently be effected by using a sight box comprising a transparent screen which does not itself provide a complete seal against contamination but in combination with an air curtain, for example provided by a laminar air flow unit, provides an effective seal or screen against contamination whilst permitting transport of packaging materials into the sterile workspace without requiring devices such as air locks.

All materials entering the region enclosed within the air curtain must either be sterile or be sterilized before being moved into the sterile workspace proper. The food will typically be supplied by pipe and can therefore be sterilized beforehand. Usually the packaging materials will not be supplied sterile but will be sterilized inside the air curtain. The sterilization may be performed by an irradiation technique rather than a wet or chemical technique because the former are more readily applied to continuous line production on the scale normally employed. Typically, the irradiation will be by ultra violet (U.V.) light, X or γ rays or accelerated electrons. U.V. radiation is preferred in the present invention, because it can be highly effective and the radiation shielding problems are less than in the other systems.

Where continuous line packaging of for example, food, is performed under aseptic conditions, problems have been met when it is necessary to perform routine maintenance or repair work within the aseptic workspace, in that it has been impractical to sterilize the necessary tools and utilities which have to be used in the aseptic workspace. Typical problems on, for example, milk food packaging lines arise from spillage or overfilling of the containers, or collapse of a container (which are typically of aluminum foil or a foil/plastics laminate) under the pressure used in hermetically sealing the cover onto it or mechanical defects. Since such foods are excellent bacterial and/or mould media, it is necessary to remove the spillage and/or any collapsed containers from the production line. Until now because such maintenance breaks the aseptic seal around the workspace, it has been necessary to re-sterilize the line each time such a fault occurs.

Under normal operating conditions the sterile utilities necessary to service the units will only be in use for a relatively short period of time compared with a production run. It is thus advantageous to be able to supply the necessary sterile utilities only when required for servicing. By making the connection between the external service unit and the workspace inside the aseptic screen detachable it is possible to provide services for several production units from one service unit.

It is an object of the present invention to provide a service unit which is capable of providing the necessary sterile utilities from a position outside the aseptic screen and is thus able to service several units.

Accordingly, the present invention provides a mobile service unit for the provision of sterile utilities, including water and pressurized air to tools within a sterile workspace within an aseptic packaging line, characterised in that the service unit is outside the sterile workspace and comprises inlets for the utilities, including water and pressurised air, means for sterilizing the utilities and outlets including detachable couplings adapted to connect the sterile utilities, corresponding inlets adjacent but exterior the sterile workspace and connected without loss of sterility to tools operable within the workspace and manipulable from outside the workspace, whereby to provide the sterile utilities including water and pressurized air to the tools within the workspace.

In addition to sterile water and air, it is desirable to include a supply of disinfectant, for example, as a spray of liquid to ensure positive asepsis in the workspace and to provide a means for removing waste fluids and debris from the workspace after servicing. This can conveniently be done by a suction line to the service unit. Further, it is convenient to include both sterile hot and cold water.

Further features of the invention appear from the following description of a typical example in conjunction with the attached drawings. Here:

FIGS. 3 to 5 give the principal views of a servicing unit.

Figure 1:
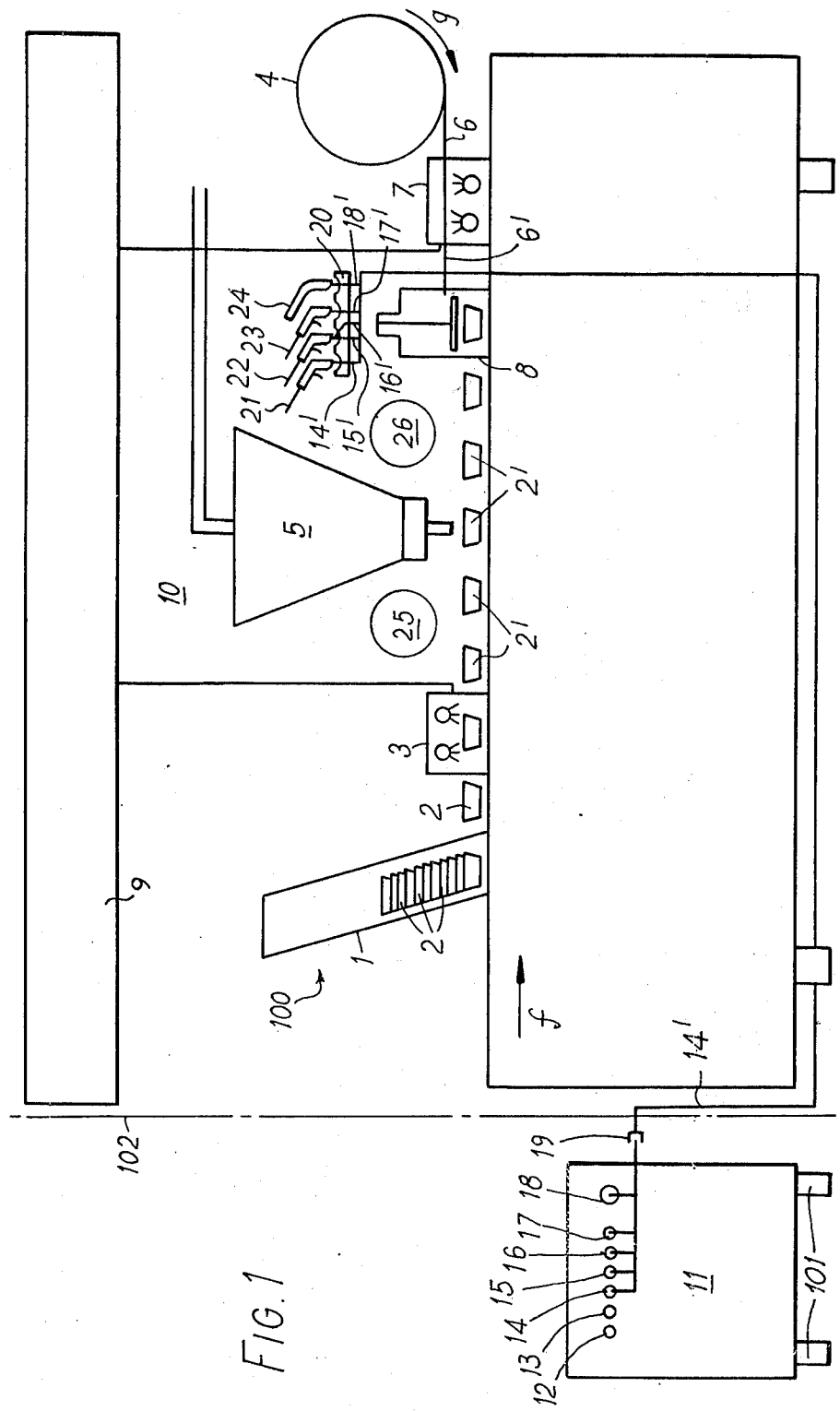
FIG. 1 shows diagrammatically a packaging machine operated in sterile atmosphere and a supply servicing unit placed outside the sterile atmosphere in accordance with the invention.

A food packaging machine operated in an atmosphere that is largely kept germ-free has in FIG. 1 the reference number 100.

The plant 100 comprises a packaging line with stations, which are described below, progressing in the direction f in which containers 2 for food are moved.

The packaging plant 100 (as viewed in FIG. 1), has on the left a stacking device 1 from the bottom end of which containers 2 are taken at the fixed-cycle operation rate of the packaging line. At 3 there is a sterilization unit, e.g., a UV irradiation unit, for the containers 2, which are thus made germ-free. The irradiated containers 2' then pass through a filling station 5 where they are filled with food or the like under sterile conditions.

6 is a cover foil which can be unwound from a coiler 4 in the direction of arrow g. The cover foil is passed through a sterilization unit, e.g., a UV irradiation unit, 7 to a punching and sealing station 8. Lids are here punched from the irradiated foil 6' and sealed on to the irradiated containers 2'.

9 is a laminar flow unit which keeps the space 10 (screened by a plexiglass sight cabin) for the packaging plant 100 sterile.

A mobile supply servicing unit 11 on wheels 101 is arranged in the normal atmosphere outside the sterile space 10. The transparent partition between the sterile space 10 and the outer environment is indicated by dash-dot line 102. The servicing unit 11 has mains connections 12 and 13 for water and compressed air, outlet connections 14 to 17 for sterilized hot water, disinfectants, sterilized compressed air for atomizing the disinfectant, and sterilized compressed air as well as a suction ventilator connection 18. The connections 14 to 18 are joined, across plug-in couplings 30 t0 33, 43 situated outside the screened space 10, to lines which have the same but ticked (') reference numbers as connections 14 to 18. Lines 14' to 18' lead to a holding device 20 for a hot-water spray gun 21, a spray gun 22 with connections to both the disinfectant line 15' and a line 16' for germ-free compressed air, a blowout gun 23 and a suction nozzle 24.

Guns 21 and 23 and the suction nozzle 24 are hand-operated. Gauntlets extending into the sterile space 10 at 25 and 26 are sealed in thereby constituting a glove box, and the tools 21 to 24 can thus be handled by an operator without breaking the seal between the sterile space 10 and the environment.

The operator can thus undertake maintenance work in the sterile space 10 without changing the germ-free atmosphere in it. For instance, if a container 2' is overfilled irregularly or contents are spilled, the surplus material can be removed under germ-free conditions, any displaced containers can be placed in position, and both containers and plant components can be cleaned under germ-free conditions. It is clear that setting and control operations can likewise be carried out in space 10 without altering the sterile atmosphere.

When such servicing or maintenance work is completed the servicing unit 11 can be disconnected from the packaging plant by releasing the plug-in couplings 19 and moved to another plant for similar or different servicing or maintenance operations.

Figure 2:
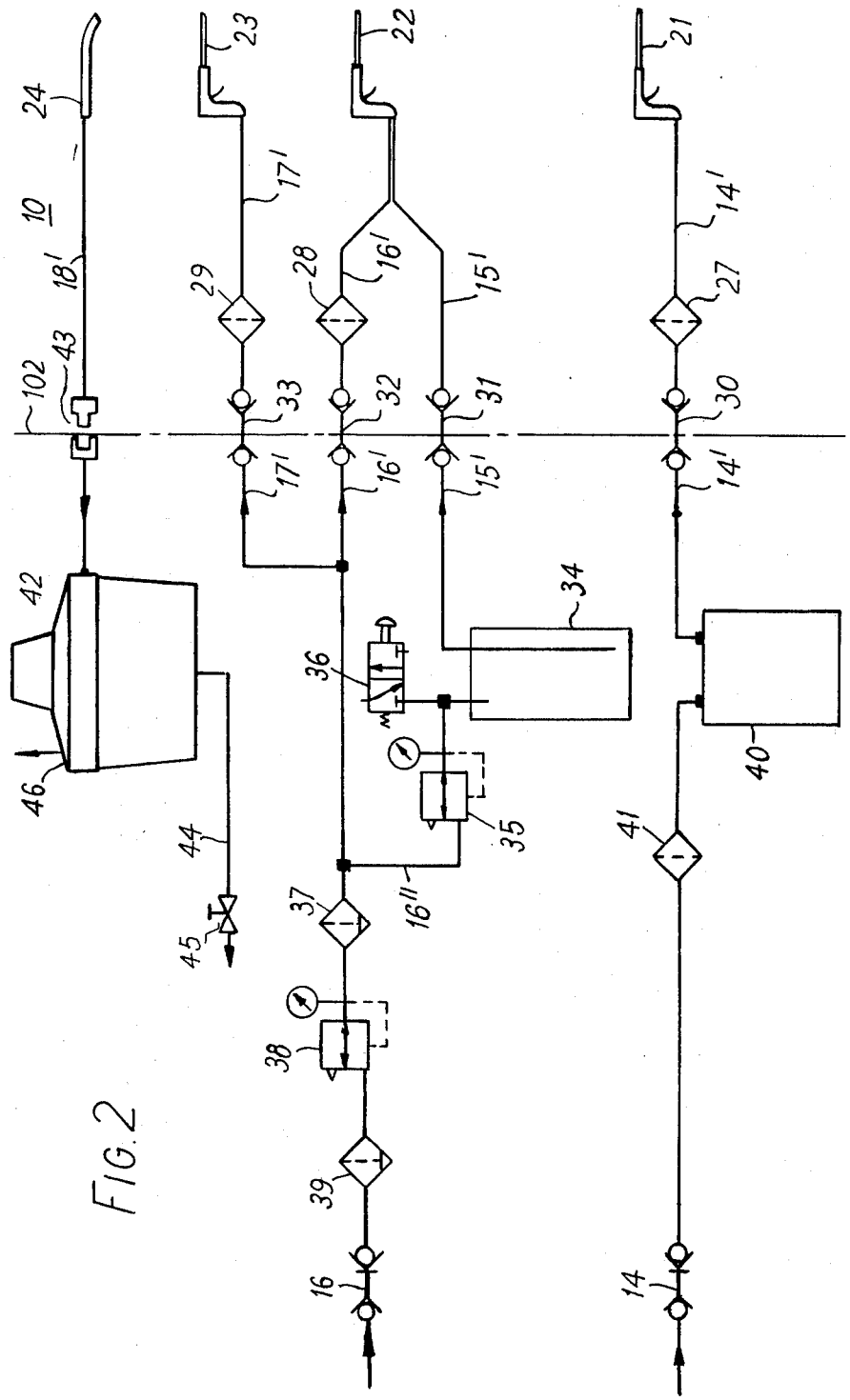
FIG. 2 is a connection diagram of a servicing unit in accordance with the invention.

FIG. 2 likewise indicates by a dash-dot line the sight cabin 102 which separates the sterile space 10 from the environment.

The hot-water gun 21, disinfectant spray gun 22 and the blow-out gun 23 are connected to the rapid-closure couplings 30, 31, 32 and 33 via sterile filters 27, 28, 29; as for the two lines 15' and 16' which both lead to gun 22, a sterile filter 28 is installed only in line 16' with the germ-free compressed air, since such a filter un unnecessary in line 15' with the disinfectant.

Disinfectants are introduced through line 15' from a tank 34 which is slightly pressurized through a branch line 16" of the air pressure line 16' via a pressure reducing valve 35. Moreover, ventilation 36 is provided for the tank.

A filter 37, a pressure reducing valve 38 and a water separator and activated carbon filter 39 are arranged before line 16" branches off. The purpose of these components is to sterilize the compressed air supplied through connection 16.

Line 17" branches off line 16' and takes germ-free compressed air to the blow-out gun 23 via the rapid-closure coupling 33 and a sterile filter 29.

The hot water is taken to the rapid-closure coupling 30 from a water boiler 40 which is fed from the mains connection 14 across a sterile filter 41.

Finally, a water exhaust 42 is provided, which is connected to the suction nozzle 24 through line 18' and plug-in coupling 43. The liquid is taken from the water exhaust through a line 44 into which a drain valve 45 is installed. The waste air can escape through a ventilator opening 46.

All the parts shown in FIGS. 1 and 2 to the right of the partition 102 are inside the sterile space 10, and all those to the left of the partition are accommodated in the mobile supply service unit 11.

FIGS. 3 to 5 give an example of the design of the servicing unit 11. This unit can be moved on rollers 101 by operating a hand lever 103. Connections 12 to 18 are at the rear of this unit. On the front side is a control panel with the necessary control and adjustment organs.

The servicing unit of the invention permits maintenance operations and breakdown repair under sterile conditions. On completion of this work the packaging plant is again ready for use straight away, without the need for cleaning and sterilization on a large scale.

The plant is fool-proof and the possibility of contamination does not therefore arise.

The servicing unit is simple to operate and requires no highly qualified personnel.

It is clear that a servicing unit in accordance with the invention can be used in cases other than for sterile packaging, wherever operations are carried out in a closed space under special atmospheric conditions, e.g., those dangerous to man. It is obvious that other utilities or energy, e.g., electrical energy, can likewise be fed to tools present in the closed space via the servicing unit.

We claim:

1. The combination of an aseptic packing unit and a service unit;
   a. the aseptic packing unit comprising
      i. means for providing a sterile workspace,
      ii. sterile means within said workspace for filling previously sterilized containers with previously sterilized filling material and closing said containers, when filled, with previously sterilized lids,
      iii. means for providing a descending curtain of sterile air surrounding said sterile workspace, said curtain of air providing a barrier preventing contamination from outside said sterile workspace,
      iv. means operable within said sterile workspace for manipulation of said sterilized containers, lids for closing said containers, said sterilized filling material and said filled and closed containers,
      v. a plurality of tools comprising supply guns operable by said manipulating means to provide utilities including sterile water and sterile air within said sterile workspace without loss of sterility within said workspace,
      vi. a plurality of first detachable couplings on the exterior of said unit outside said curtain of air, and
      vii. supply lines for connecting said tools to said first detachable couplings, said supply lines including means for prevention of contamination of said tools when said first detachable couplings are detached and open to non-sterile conditions;
   b. the service unit being a mobile unit exterior to and independent from said aseptic packing unit and said sterile workspace, said service unit comprising
      i. a plurality of inlets, for utilities including water and air,
      ii. means for sterilizing said utilities,
      iii. a plurality of outlets including second detachable couplings adapted to connect to corresponding ones of said first detachable couplings on said aseptic packing unit thereby supplying said tools with said utilities without loss of sterility, and iv. a suction pump within said service unit to exhaust a waste line from said sterile workspace;

c. said first and second detachable couplings being co-acting sets of quick-acting plug-in, non-return couplings.

2. The combination of claim 1 wherein the utilities include a means for providing a supply of disinfectant and hot and cold sterile water and said service unit includes means for heating said hot water.

3. The combination of claim 1 wherein said manipulating means comprises a glove box.

* * * * *